US012613172B2

(12) United States Patent (10) Patent No.: US 12,613,172 B2
Yim et al. (45) Date of Patent: Apr. 28, 2026

(54) METHOD FOR ESTIMATING ELASTIC CONSTANTS OF ANISOTROPIC MATERIAL

(71) Applicant: SEOUL NATIONAL UNIVERSITY R&DB FOUNDATION, Seoul (KR)

(72) Inventors: Ju-Hyi Yim, Seoul (KR); Ki-Bok Min, Gyeonggi-do (KR); Seung-Ki Hong, Seoul (KR); Yoon-Sung Lee, Seoul (KR)

(73) Assignee: SEOUL NATIONAL UNIVERSITY R & DB FOUNDATION, Seoul (KR)

( * ) Notice: Subject to any disclaimer, the term of this patent is extended or adjusted under 35 U.S.C. 154(b) by 384 days.

(21) Appl. No.: 18/571,560

(22) PCT Filed: Jun. 13, 2022

(86) PCT No.: PCT/KR2022/008310
§ 371 (c)(1),
(2) Date: Dec. 18, 2023

(87) PCT Pub. No.: WO2022/265324
PCT Pub. Date: Dec. 22, 2022

(65) Prior Publication Data
US 2024/0288349 A1 Aug. 29, 2024

(30) Foreign Application Priority Data

Jun. 17, 2021 (KR) ........................ 10-2021-0078932

(51) Int. Cl.
*G01N 3/08* (2006.01)
*E21B 49/02* (2006.01)
(Continued)

(52) U.S. Cl.
CPC .............. *G01N 3/08* (2013.01); *G01N 3/066* (2013.01); *G01N 33/24* (2013.01); *E21B 49/02* (2013.01);
(Continued)

(58) Field of Classification Search
CPC .......... G01N 3/08; G01N 3/066; G01N 33/24; G01N 3/00; E21B 49/02; G01V 1/30;
(Continued)

(56) References Cited

U.S. PATENT DOCUMENTS

| | | | |
|---|---|---|---|
| 7,751,980 B2 | 7/2010 | Yan et al. | |
| 2017/0299485 A1 | 10/2017 | Lai et al. | |
| 2021/0173976 A1* | 6/2021 | Ma ........................... | G01V 3/10 |

FOREIGN PATENT DOCUMENTS

| | | |
|---|---|---|
| CN | 105628486 B | 4/2019 |
| JP | H07-294408 A | 11/1995 |

(Continued)

OTHER PUBLICATIONS

Leighton Watson et al., "Resonant ultrasound spectroscopy of horizontal transversely isotropic samples", Journal of Geophysical Research: Solid Earth, Jun. 8, 2015, pp. 1-11.
(Continued)

*Primary Examiner* — Peter J Macchiarolo
*Assistant Examiner* — John M Royston
(74) *Attorney, Agent, or Firm* — Renner, Otto, Boisselle & Sklar, LLP

(57) ABSTRACT

The present disclosure provides a method for estimating the elastic constants of an anisotropic material such as aniso-tropic rocks such as gneiss and shale even when using a general loader, the method enabling anisotropic elastic con-stants to be estimated even with only a single core sample, thereby significantly reducing time and costs.

15 Claims, 9 Drawing Sheets

(51) Int. Cl.

| | | |
|---|---|---|
| *G01N 3/00* | (2006.01) |
| *G01N 3/06* | (2006.01) |
| *G01N 33/24* | (2006.01) |
| *G01V 1/30* | (2006.01) |
| *G01V 1/46* | (2006.01) |
| *G01V 1/50* | (2006.01) |

(52) U.S. Cl.
CPC .................. *G01N 3/00* (2013.01); *G01V 1/30* (2013.01); *G01V 1/306* (2013.01); *G01V 1/46* (2013.01); *G01V 1/50* (2013.01); *G01V 2210/586* (2013.01); *G01V 2210/626* (2013.01)

(58) Field of Classification Search
CPC . G01V 1/46; G01V 1/50; G01V 1/306; G01V 2210/586; G01V 2210/626
USPC .......................................................... 73/774
See application file for complete search history.

(56) References Cited

FOREIGN PATENT DOCUMENTS

| | | |
|---|---|---|
| JP | 2005-265738 A | 9/2005 |
| JP | 2012-173064 A | 9/2012 |
| KR | 10-2015-0076390 A | 7/2015 |
| KR | 10-2017-0092830 A | 8/2017 |
| KR | 10-2209605 B1 | 1/2021 |

OTHER PUBLICATIONS

Every, A.G. et al., 'Determination of the elastic constants of anisotropic solids from acoustic-wave group-velocity measurements', Physical Review B, Nov. 1, 1990, vol. 42, No. 13, pp. 8196-8205.

Jung-Woo Cho et al., "Deformation and strength anisotropy of Asan gneiss, Boryeong shale, and Yeoncheon schist", International Journal of Rock Mechanics & Mining Sciences 50, Jan. 5, 2012, pp. 158-169.

Morteza Nejati et al., "A methodology to determine the elastic properties of anisotropic rocks from a single uniaxial compression test", Journal of Rock Mechanics and Geotechnical Engineering 11, Jul. 27, 2019, pp. 1166-1183.

Chulwhan Park et al., "A model Study on Deformability of a Transversely Isotropic Rock" Tunnel & Underground Space, Journal of Korean Society for Rock Mechanics, vol. 18, No. 4, pp. 252-262.

Chulwhan Park, "Anlysis of Elastic Constants of an Anisotropic Rock", Tunnel & Underground Space, Journal of Korean Society for Rock Mechanics, vol. 11, No. 1, 2001, pp. 59-63.

International Search Report and Written Opinion corresponding to counterpart International Patent Application PCT/KR2022/008310 mailed Sep. 8, 2022, English translation.

* cited by examiner

[FIG. 1]
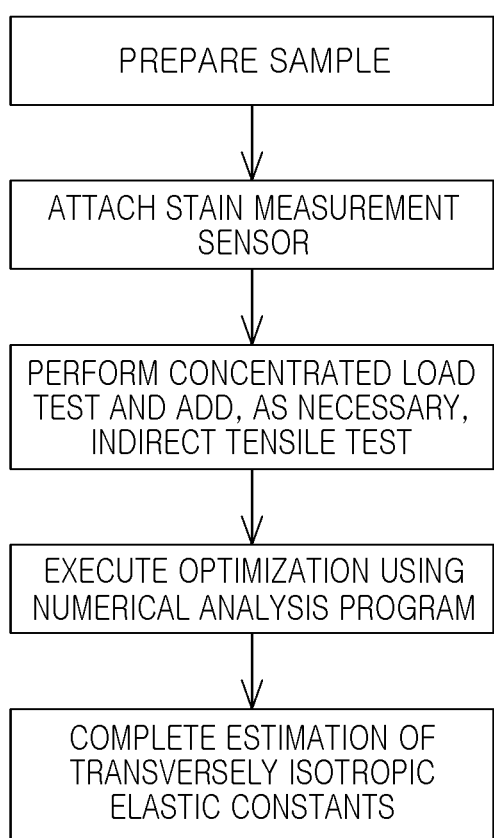

[FIG. 2a]
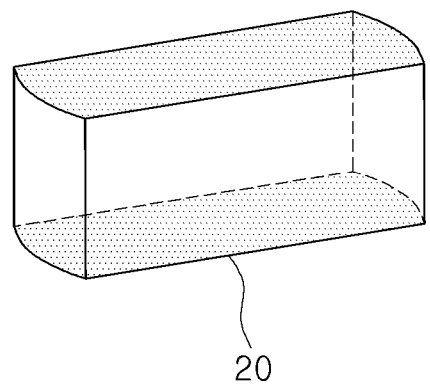
20
[FIG. 2b]
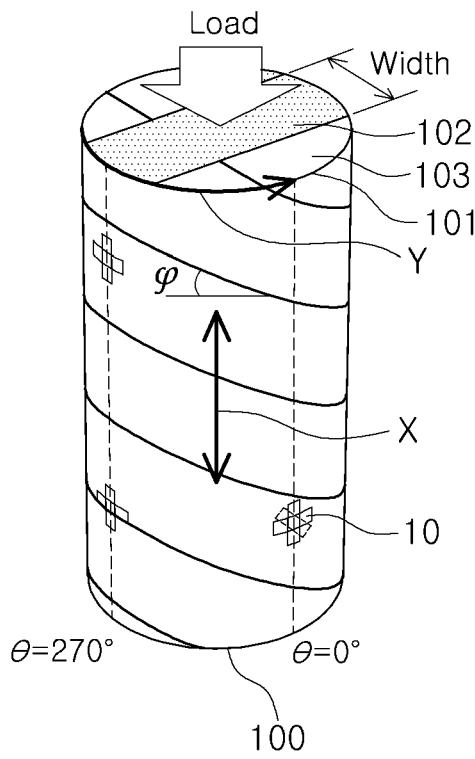
100

[FIG. 2c]
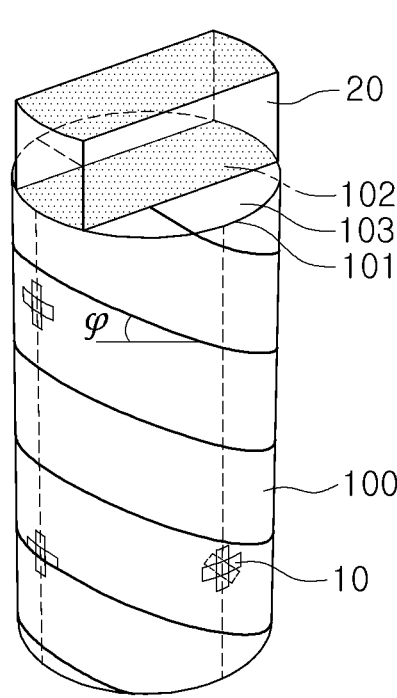

[FIG. 3]
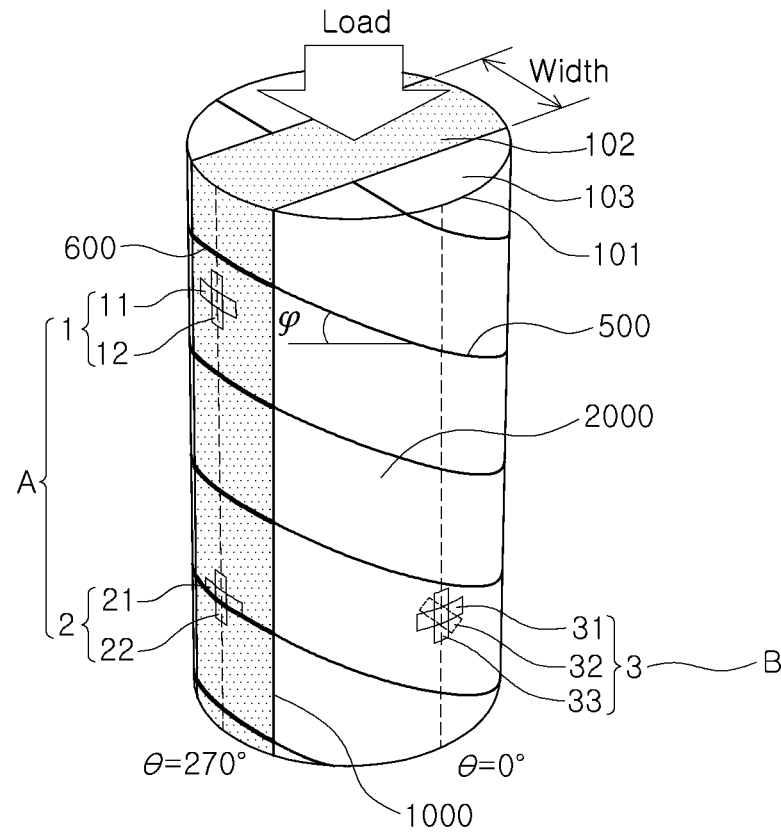

[FIG. 4]
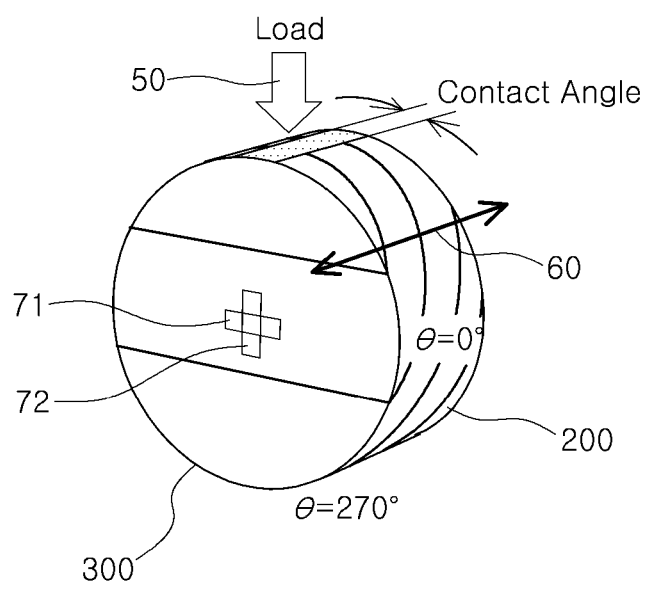
[FIG. 5a]
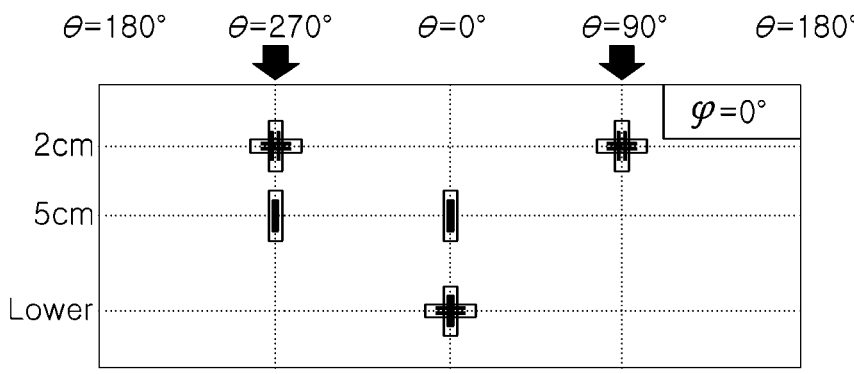

[FIG. 5b]
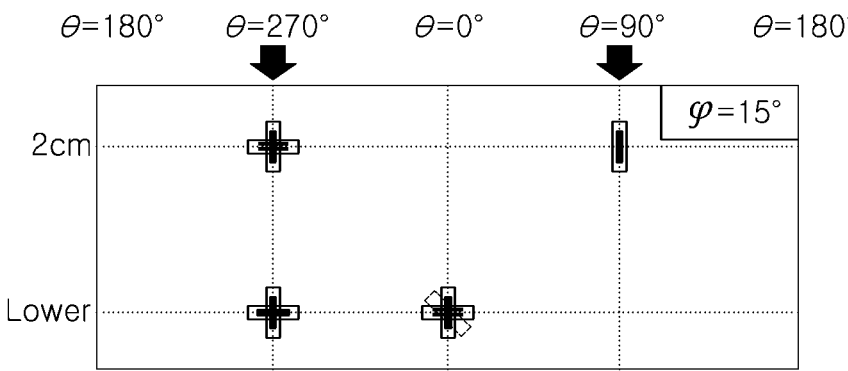
[FIG. 5c]
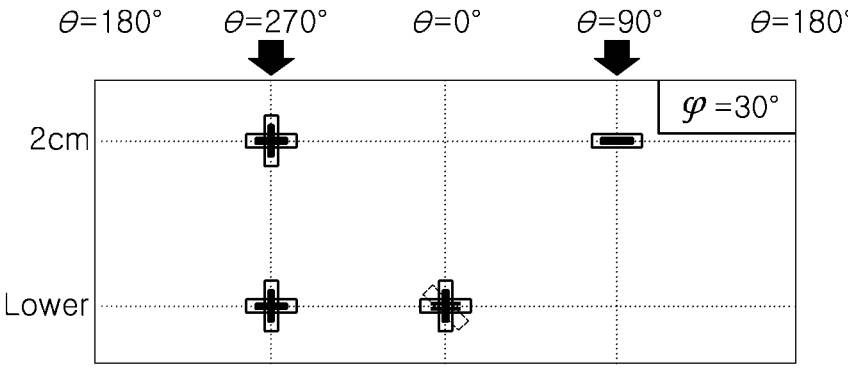
[FIG. 5d]
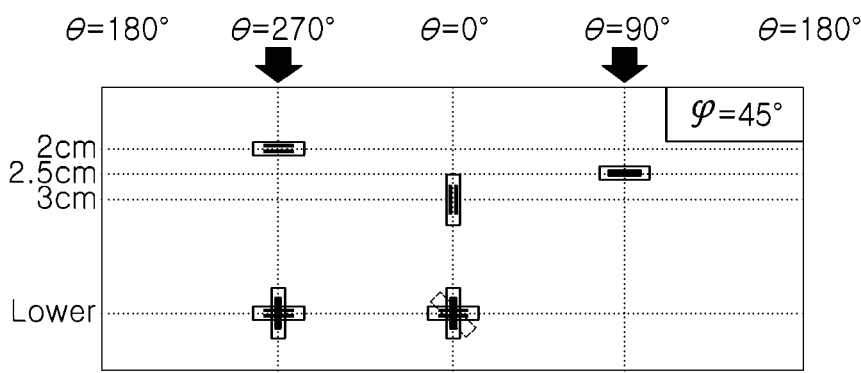

[FIG. 5e]
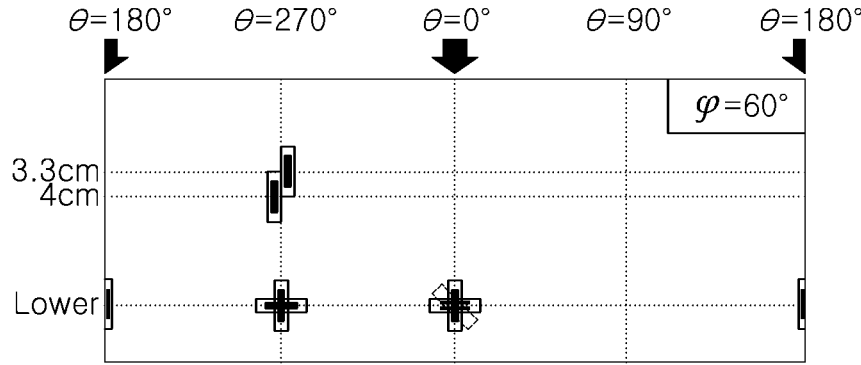
[FIG. 5f]
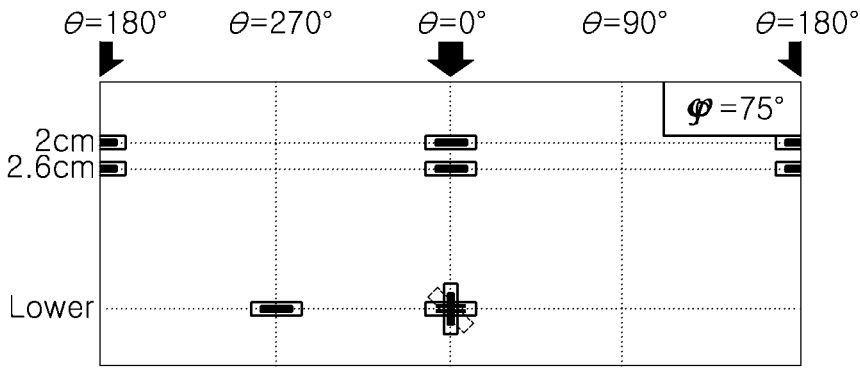
[FIG. 5g]
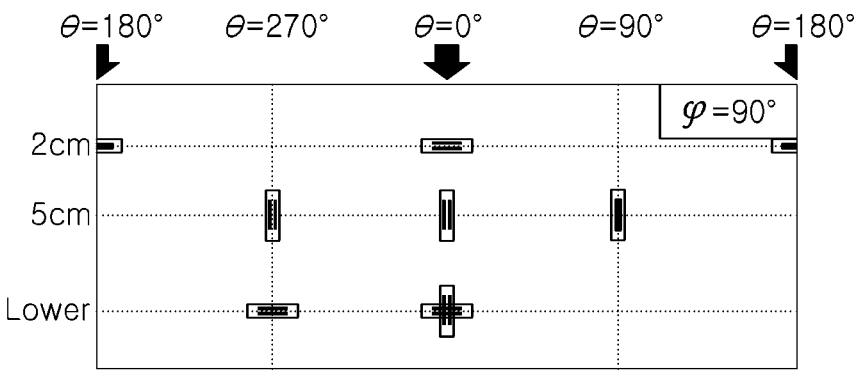

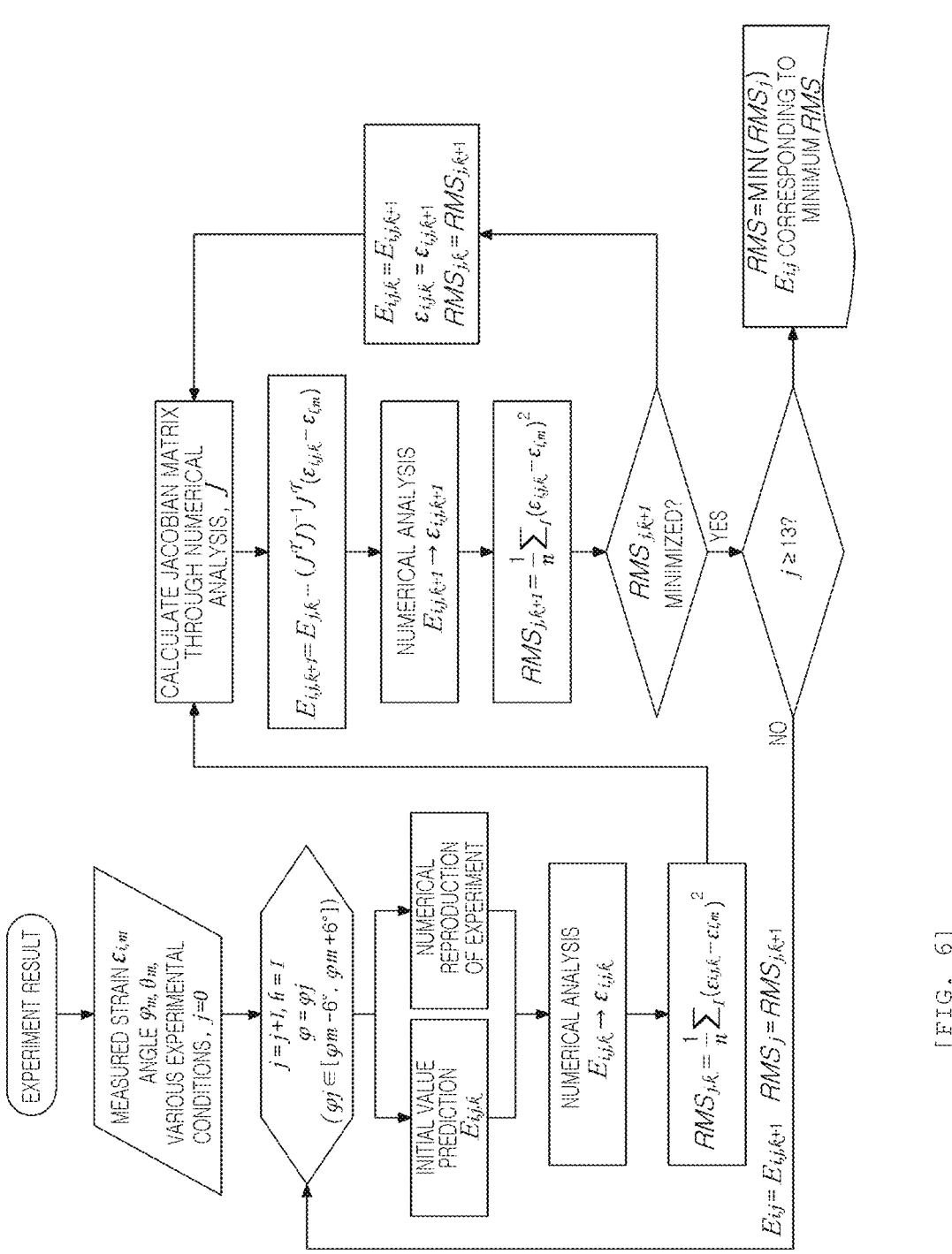
[FIG. 6]

[FIG. 7]
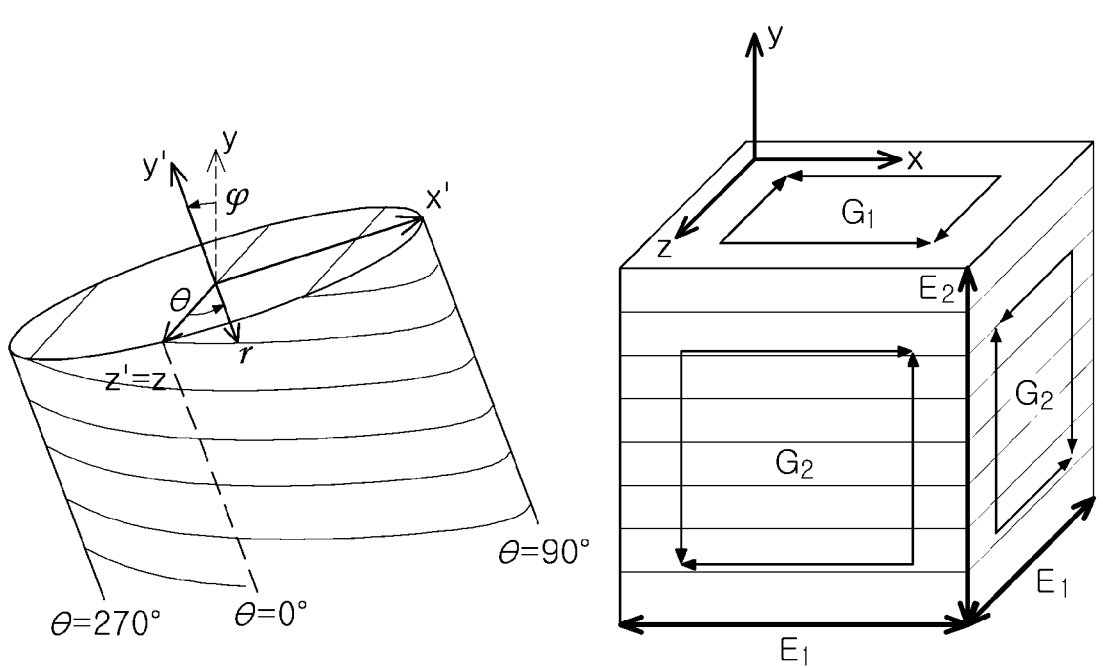

METHOD FOR ESTIMATING ELASTIC CONSTANTS OF ANISOTROPIC MATERIAL

This application is a national phase of International Application No. PCT/KR2022/008310 filed Jun. 13, 2022, which claims priority of Republic of Korea Application No. 10-2021-0078932 filed Jun. 17, 2021, each of which is hereby incorporated herein by reference in its entirety.

TECHNICAL FIELD

The present disclosure relates to a method for estimating elastic constants of an anisotropic material.

BACKGROUND ART

Anisotropic rocks such as gneiss and shale exist in various strata, and industries in various resource fields target these strata. Shale, a representative anisotropic rock, includes a large amount of shale gas, and the size of the global market for shale gas was evaluated at $68.9 billion in 2019 (Grand View Research, 2020). Furthermore, research is being conducted to build a high-level radioactive waste disposal system in a deep underground around the world, including countries such as Finland, Sweden, Korea and the like, and geothermal energy and carbon dioxide underground storage are also growing industrially. In order for these technologies to be further advanced, a detailed understanding of ground layers is required.

Specifically, it may be greatly advantageous to understand information about elastic constants of the rock that forms the ground in order to design drilling methods and conditions in these technologies. However, rocks often have anisotropy in which an elastic constant value thereof varies, depending on the direction, and accordingly, an overall physical behavior of the rock mass may be understood only when the elastic constants of the rock are measured in various directions. Previously, in order to measure the elastic constants by the direction of the rock, a core sample had to be collected from a plurality of directions and the elastic constants had to be measured using the collected cores in each direction, or in order to measure the elastic constants in various directions in one core, it was necessary to use a special loading machine. Accordingly, there was a problem that an application of these methods involved considerable costs, but until now, no technology has been developed at a level that can effectively reduce time and costs.

(Patent Document 1) Patent Publication No. 10-2017-0092830

SUMMARY OF INVENTION

Technical Problem

An aspect of the present disclosure is to provide a method for estimating anisotropic elastic constants for an anisotropic material that can significantly reduce time and costs by estimating anisotropic elastic constants with only a single core sample.

The object of the present disclosure is not limited to the above-described contents. Anyone skilled in the art to which the present disclosure pertains will have no difficulty in understanding the additional problems of the present disclosure from an overall content of the specification of the present disclosure.

Solution to Problem

According to an aspect of the present disclosure, provided is a method for estimating elastic constants, the method including:
    collecting a core sample from an anisotropic material;
    applying a load to respective ends of the core sample;
    measuring a strain value on a surface of the core sample to which the load is applied;
    calculating a strain in the same position as a position in which the strain was measured by performing a computer numerical simulation test under the same load condition applied to a core sample while changing an input elastic constant value; and
    determining an elastic constant value when an error between the measured strain and the calculated strain is the lowest, as an elastic constant value of the core sample,
    wherein at least one of the load applied to respective ends of the core sample is a concentrated load applied only to a portion of a surface of an end.

According to an aspect of the present disclosure, provided is a method for estimating elastic constants,
    including:
    collecting a core sample from an anisotropic material;
    applying a load to respective ends of the core sample;
    measuring a strain value on a surface of the core sample to which the load is applied;
    calculating a strain in the same position as a position in which the strain was measured by performing a simulation test under the same load computer condition applied to a core sample while changing an input elastic constant value; and
    determining a value of an elastic constant obtained when the error between the measured strain and the calculated strain falls within an allowable range, as an elastic constant value of the core sample,
    wherein at least one of the load applied to respective ends of the core sample is a concentrated load applied only to a portion of a surface of an end.

Advantageous Effects of Invention

According to an aspect of the present disclosure, provided is a method for estimating elastic constants of an anisotropic material, the method enabling anisotropic elastic constants to be estimated even with a single core sample, thereby significantly reducing time and costs.

Advantages and effects of the present application are not limited to the foregoing content and may be more easily understood in the process of describing a specific example embodiment of the present disclosure.

BRIEF DESCRIPTION OF DRAWINGS

FIG. 1 schematically illustrates an order of a method for measuring elastic constants for an anisotropic material according to an aspect of the present disclosure.

FIG. 2 is a schematic diagram that schematically shows a method for measuring elastic constants through a concentrated load test, which is an embodiment of the present disclosure, and FIG. 2A illustrates a structure of a soft loading plate, FIG. 2B illustrates a concentrated load test method for a core sample, and FIG. 2C illustrates a structure in which a soft loading plate is disposed on one end of the core sample so as to come into contact with only contacts a portion of a surface of one end of the core sample.

FIG. 3 illustrates a schematic diagram of the core sample during a concentrated load test.

FIG. 4 is a schematic diagram schematically illustrating a method for measuring an indirect tensile test according to an embodiment of the present disclosure.

FIG. 5 illustrates an attachment position of a strain measurement sensor during a concentrated load test, which is an embodiment of the present disclosure.

FIG. 6 schematically illustrates a flowchart for determining an elastic constant value through a computer numerical simulation test, which is an embodiment of the present disclosure.

FIG. 7 illustrates a conceptual diagram of an elastic constant and a direction of an isotropic plane, which is an embodiment of the present disclosure.

BEST MODE FOR INVENTION

The terms used in the present specification are intended to describe specific embodiments and are not intended to limit the present disclosure. In addition, singular forms used in the present specification include plural forms unless the relevant definition indicates the opposite meaning.

The meaning of "include" and "comprise" used in the specification specifies the configuration and does not exclude the existence or addition of other configurations.

Unless otherwise defined, all terms including technical and scientific terms used herein have the same meaning as commonly understood by one of ordinary skill in the art to which example embodiments of the present disclosure belong. It will be further understood that the terms, such as those defined in commonly used dictionaries, should be interpreted as having meanings consistent with the relevant technical literature and the currently disclosed content.

Hereinafter, preferred embodiments of the present disclosure will be described. However, embodiments of the present disclosure may be modified into various different forms, and the scope of the present disclosure is not limited to embodiments described below. Furthermore, embodiments of the present disclosure are provided to more fully explain the present disclosure to those who have average knowledge in the art.

Conventional methods for obtaining elastic constants of anisotropic rocks have engineering and economic limitations in practical application. Specifically, existing methods have limitations such as requiring two or more core samples collected from various directions or requiring the use of a special loading machine to estimate elastic constants of anisotropic rocks, and thus, there may be a problem in that costs are significantly increased.

Accordingly, as a result of intensive study to solve the above-mentioned problem, the present inventors developed a method that can sufficiently calculate elastic constants of an anisotropic material even when using a general loading machine and only a single core sample, and have completed the present disclosure.

Specifically, according to an aspect of the present disclosure, a method for estimating elastic constants of an anisotropic material, includes:

collecting a core sample from an anisotropic material;

applying a load to respective ends of the core sample;

measuring a strain value on a surface of the core sample to which the load is applied;

calculating a strain in the same position as a position in which the strain was measured by performing a computer numerical simulation test under the same load condition applied to a core sample while changing an input elastic constant value; and determining an elastic constant value when an error between the measured strain and the calculated strain is the lowest, as an elastic constant value of the core sample, and at least one of the load applied to respective ends of the core sample is a concentrated load applied only to a portion of a surface of an end.

According to another aspect of the present disclosure, a method for estimating elastic constants of an anisotropic material, includes:

collecting a core sample from an anisotropic material;

applying a load to respective ends of the core sample;

measuring a strain value on a surface of the core sample to which the load is applied;

calculating a strain in the same position as a position in which the strain was measured by performing a computer numerical simulation test under the same load condition applied to a core sample while changing an input elastic constant value; and determining a value of an elastic constant obtained when the error between the measured strain and the calculated strain falls within an allowable range, as an elastic constant value of the core sample, and at least one of the load applied to respective ends of the core sample is a concentrated load applied only to a portion of a surface of an end.

An order of a method for estimating elastic constants of an anisotropic material is schematically illustrated in FIG. 1, and the configuration of the present disclosure will be described in detail below.

First, a core sample is collected from an anisotropic material. The anisotropic material includes a material such as anisotropic rocks such as gneiss and shale. In addition, the core sample may be collected using a coring method well known in the art, and may have a columnar shape. A columnar cross-section is not particularly limited, but may have a circular shape due to the characteristics of the coring method. However, the shape is not necessarily limited to a circular shape, and may have various cross-sections due to a change in a collection method or post-processing. Furthermore, the columnar shape described in the present disclosure generally denotes a shape having a longer length than a width, and is not limited as long as it can be recognized as a columnar shape in the technical field.

Furthermore, the core sample described in the present disclosure is not limited to the shape, and may be applied to various types of samples. As long as the test of core sample can be accurately reproduced by computer simulation described below, a method for estimating elastic constants according to the present disclosure may be applied to core samples of various shapes and sizes, without being particularly limited to the shape and size of the core sample.

According to the present disclosure, in estimating the elastic constant from the anisotropic material, as the core sample, the elastic constant may be obtained using only a single (i.e., one) core sample. Accordingly, in the present disclosure, the elastic constant may be sufficiently obtained using only a sample collected in one direction, and since the present disclosure do not require two or more core samples collected in various directions as in the existing methods, time and costs may be greatly reduced.

Subsequently, a load is applied to the collected core sample. The loads may be applied to respective ends of the core sample. In this case, at least one of the load applied to respective ends of the core sample may be a concentrated load applied only to a portion of the end surface, not the entire end surface.

Generally, the strain is measured while applying a uniform load to an entire cross section of the sample, and in this case, because the same stress state is applied to all positions of the material, when measuring the elastic constants for each direction of the material, it was necessary to perform two or more tests by changing the measurement direction. However, when a concentrated load is applied as in the present disclosure, a different stress state is formed for each position of the material, and thus, even in the case of a single anisotropic material, it may be possible to easily obtain elastic constants for each direction.

Meanwhile, according to one example of the present disclosure, for example, as illustrated in FIG. 2C, a soft loading plate 20 may be provided so as to come into contact with only a portion of an end surface to which the load is applied. Accordingly, since the soft loading plate 20 partially occupies an end surface 101 (i.e., a surface of a core sample 100 in an axial direction (X-direction)), the end surface 101 of the core sample 100 has a region 102 in contact with the soft loading plate 20 and a region 103 not in contact with the soft loading plate.

In this case, the end surface 101 refers to a surface of a sample viewed in a direction of applying a load to the core sample, and in this specification, the axial direction (X-direction) may be identical to a direction in which the load is applied to the core sample during a concentrated load test (except for an indirect tensile test) (corresponding to a 'Load' in FIG. 2).

According to an embodiment of the present disclosure, although the soft loading plate 20 is not particularly limited, materials with a Young's modulus lower than that of the sample, but yield stress similar or greater than that of the sample (i.e., yield stress greater than or equal to an anisotropic material) are used. If the above-described conditions are satisfied, a material of the soft loading plate is not particularly limited, but since the soft loading plate is easily manufactured into a desired shape in a 3D printing method, in an example, the soft loading plate may be formed of a material used as a material substance for a 3D printer. Veroclear may be selected and used as an example that can be advantageously used as a soft loading plate. By utilizing the soft loading plate that satisfies these conditions, it may be possible to transfer a uniform concentrated load to a specific part of the core sample as a load applied from a loading machine described below. For this reason, even though the soft loading plate is a concentrated load, it may be possible to effectively estimate the elastic constants of the sample by controlling the sample not to be destroyed under high stress. Furthermore, since the above-described soft loading plate is relatively inexpensive, it may be easily used to estimate the elastic constant without increasing manufacturing costs.

According to an embodiment of the present disclosure, a Young's modulus ($Y_1$) of the soft loading plate is set to $1/10$ or less compared to a Young's modulus ($Y_0$) of the core sample (i.e., $Y_1/Y_0 \leq 1/10$). For example, when considering a Young's modulus of a general rock, the above-described 3D printer material such as Veroclear or the like may be used, or a material such as PC, ULTEM™ 9085 Resin, ULTEM™ 1010 Resin, or the like may be used. When the Young's modulus of the soft loading plate exceeds $1/10$ of the Young's modulus ($Y_0$) of the core sample (i.e., when the $Y_1/Y_0$ exceeds $1/10$), as a load transferred to a contact surface becomes non-uniform, there may be a problem in that inaccuracy may increase in reproducing a test with computer numerical simulation. As a value of $Y_1/Y_0$ decreases to less than $1/10$, a load transferred in the contact area becomes homogeneous, and thus, this may be preferable in terms of numerical simulation. However, there may be a concern that a phenomenon in which a contact area increases due to a Poisson effect (a phenomenon in which the pressure plate expands laterally during a compression test) may occur. However, in the case of an test using the above-described materials such as Veroclear, ULTEM™ 9085 Resin, and ULTEM™ 1010 Resin, etc., a Poisson phenomenon was negligible, and in reality, it may be meaningless to estimate a lower limit of $Y_1/Y_0$ in that it is difficult to find a material with a Young's modulus that is much smaller than the materials such as the aforementioned Veroclear but still has a high level of yield stress. Accordingly, in the present disclosure, the lower limit of a value of $Y_1/Y_0$ is not separately limited. However, as a non-limiting example, when an allowable limit of an amount of change in a width of a pressurized area (corresponding to 'Width' in FIG. 3) is about 1 mm, a lower limit of $Y_1$ may be approximately 0.5 GPa, and a lower limit of $Y_1/Y_0$ may be approximately $1/100$.

According to an embodiment of the present disclosure, the soft loading plate 20 is provided to come into contact with only a portion of an end surface 101, but the soft loading plate 20 may be disposed differently according to a coring direction of the core sample. For example, a region in which the soft loading plate is in contact with the core sample may include a line segment connecting two points in which each of straight lines drawn towards an end surface meets the end surface at a point closest to and farthest from a surface of one end of the core sample among respective points of a curve 600 in which an isotropic plane 500 of the core sample meets a circumferential surface.

Specifically, as illustrated in FIGS. 5B to D, when the coring direction φ of an x-axis is greater than 0° and less than or equal to 45°, as illustrated in FIG. 3 of the present disclosure, the soft loading plate 20 may be disposed side by side, on a region 1000 in which a curve 600 in which an isotropic plane 500 of the core sample meets the circumferential surface of the sample (i.e., surfaces other than both end surfaces of the core sample) is parallel to the end surface 101 of the sample. In addition, as illustrated in FIGS. 5E to F, when the coring direction φ of the x-axis is greater than 45° and less than or equal to 90°, the soft loading plate 20 may be disposed side by side on a region in which the curve 600 has a maximum slope.

Furthermore, as illustrated in FIG. 5A, when the coring direction φ is 0°, because the entire curve 600 is parallel to the end surface 101, in this case, the soft loading plate 20 may be disposed on the end surface 101 of the core sample in an arbitrary direction.

On the other hand, as illustrated in FIG. 5G, when the coring direction φ is 90°, an area in which the soft loading plate is in contact with the core sample may include a line segment connecting two points in which the curve 600, in which the isotropic plane 500 of the core sample meets the circumferential surface of the sample, meets a surface of one end of the core sample. That is, the soft loading plate 20 may be disposed on the end surface 101 of the core sample in a direction parallel to the line segment connecting two points in which the curve 600, in which meeting the isotropic plane 500 of the core sample meets the circumferential surface of the sample, meets a surface of one end of the core sample. Accordingly, when the soft loading plate 20 is disposed on the end surface 101 of the sample, a center of a region 102 in which the end surface 101 of the core sample 100 is in contact with the soft loading plate 20 may coincide with a center of the end surface 101 of the sample.

Then, a strain value on the surface of the core sample to which the load is applied is measured. As one method of measuring the strain value, there is a method for measuring a strain value after attaching two or more strain measurement sensors in which at least one (one or more) of an attachment position and an attachment direction is different from each other, to a collected core sample. The strain measurement sensor is also referred to as a strain gauge and refers to a device attached to the surface of a core sample to measure the strain at that point. In the present disclosure, in order to explain the attachment position of the strain measurement sensor, FIG. 2B schematically illustrates a form in which the strain measurement sensor 10 is attached to the core sample 100.

According to an embodiment of the present disclosure, as illustrated in FIG. 2B, the strain measurement sensor 10 is attached to two or more points so that one or more of the attachment position and the attachment direction is different from each other on a surface except for both end surfaces of the core sample 100, and thus, a strain value at the attachment point may be measured.

Alternatively, if the core sample is cylindrical, the strain measurement sensors 10 are attached to two or more points on the surface in a circumferential direction (Y-direction) except for both end surfaces of the core sample 100, respectively, and it may be possible to measure the strain value at the attachment point. That is, the measurement of the strain value may be applied to the surfaces of both ends to which the load is applied, and may be applied anywhere on the surface of the core sample as long as it does not impair the object of the present disclosure.

In this case, two or more strain measurement sensors 10 attached to the two or more points may be attached to the same area on the surface of the core sample 100 in different measurement directions, and may be attached to two or more different points on the surface of the core sample 100, respectively.

According to an embodiment of the present disclosure, in order to produce a relatively high-accuracy elastic constant for an anisotropic material with only a single core sample, an attachment position of the strain measurement sensor and the number of strain measurement sensors may be controlled.

According to an embodiment of the present disclosure, there may be a plurality of strain measurement sensors attached to the surface of the core sample (i.e., two or three or more), and the plurality of strain measurement sensors may have at least one of an attachment position and an attachment direction different from each other.

However, since the accuracy of the number of strain measurement sensors increases as the value thereof increases, and accordingly, an upper limit of the number of strain measurement sensors may not be separately limited. However, in an example, the number of strain measurement sensors may be used up to 200 under the assumption that Kyowa's strain gauges, which are 16 mm long and 5.2 mm wide, are tightly attached to the surface of the sample when used on a sample with a diameter of 54 mm and a height of 108 mm. However, since the number of channels corresponding to sensors of a data acquisition system used in actual tests is usually several to dozens, the number thereof may be determined to be less than 100.

Furthermore, according to an embodiment of the present disclosure, in order to improve the accuracy of the elastic constant, there may be two or more positions, more preferably three or more, to attach a strain measurement sensor to the surface of the core sample.

According to an embodiment of the present disclosure, when the strain measurement sensor 10 is attached, one or more strain measurement sensors 11 or 12 may be attached to a first position 1 a certain distance away in the axial direction (X-direction) from the end surface 101 of the core sample (or a surface on a side with which the soft loading plate for the core sample is in contact). In an embodiment of the present disclosure, the strain measurement sensor 11 or 12 may be attached to the first position that is 0.5 times or more the width of the soft loading plate 20 (corresponding to "Width" in FIG. 3) and 1.5 times or less the diameter of the core sample from the end surface 101 of the core sample. In this case, the width of the soft loading plate 20 may refer to the shortest distance on a narrow side based on an area in which the soft loading plate 20 is in contact with the end surface 101 of the core sample.

On the other hand, when the first position is less than 0.5 times the width of the soft loading plate 20 (corresponding to 'Width' in FIG. 3) from the end surface of the core sample, due to testing errors, there may be a problem that the nonuniformity of the load transmitted by the soft loading plate greatly affects the strain, and when the first position is more than 1.5 times the diameter of the core sample, as the effect of the concentrated load is dispersed, there may be a problem that the accuracy of estimating the elastic constant is lowered.

Then, one or more additional strain measurement sensors 21 or 22 may be attached to a second position 2 farther from the end surface 101 in the axial direction (X-direction) than the first position. As described above, the strain value for each point measured by the strain measurement sensor attached to two or more different points may be used to estimate the elastic constant for a core sample, which is an anisotropic material to be described below.

An embodiment for an attachment form of the strain measurement sensor described above is illustrated in FIG. 3. As may be seen from FIG. 3, according to one embodiment of the present invention, two or more strain measurement sensors 11 and 12 having different strain measurement directions may be attached to the first position 1. Similarly, two or more strain measurement sensors 21 and 22 having different strain measurement directions may be attached to the second position 2.

Here, a difference in the direction of measurement of the strain may denote that the direction of strain that the strain measurement sensor attached to the surface of the core sample is designed to measure is different. In an example, when using a strain gauge as a strain measurement sensor, it may denote that a direction in which grids of the strain gauge are aligned is a direction of the strain designed for the strain gauge to measure, and the directions of the grids are different from each other. For example, at least one of the two or more strain measurement sensors attached to any one position (e.g., position 1) may have the same direction of measuring the strain as the axial direction (X-direction) of the core sample, and another may have the same direction of measuring the strain as a direction perpendicular to the axial direction (X-direction).

In other words, as illustrated in FIG. 3, the strain measurement sensor 11 and the strain measurement sensor 12 were attached to the first position 1 at the same distance from the end surface 101 of the core sample, but since the strain directions designed to be measured by each strain measurement sensor are different from each other, the strain measurement direction corresponds to a different example. For example, in FIG. 3, the strain measurement sensor 11 corresponds to an example in which the strain measurement direction is perpendicular to the axial direction (X-direction), and the strain measurement sensor 12 corresponds to an example in which a measurement direction of a strain is the same as (or parallel to) the axial direction (X-direction. Accordingly, in FIG. 3, the strain measurement sensors 21 and 22 are also identically attached to the second position 2, but the measurement directions of the strain are different from each other, and the strain measurement sensors 31, 32, and 33 also correspond to an example in which the attachment positions are identical, but the measurement directions of the strain are different.

On the other hand, in this specification, in a shape of attaching t sensor so that the measurement directions of the strain are different from each other at any one of the positions, the measurement directions of the strain must not be the same, and if the effect aimed at the present disclosure may be achieved through a computer numerical simulation test to be described below, various changes may be made in the measurement direction of the strain, and thus the shape thereof is not separately limited.

Furthermore, according to an embodiment of the present disclosure, (1 or more) strain measurement sensors 10 may be attached to the position A included in a region 1000 parallel to the region 102 in the axial direction (X-direction). The region 102 is the contact area between the soft loading plate 20 and the end surface 101.

Then, one or more additional strain measurement sensors may be attached to a position B (e.g., corresponding to a position 3 of FIG. 3) that is not included in the region 1000 parallel in the axial direction (X-direction) to the contact area 102 between the soft loading plate 20 and the end surface 101. That is, the position B may be disposed on a surface of the circumferential direction (Y-direction) of a region 2000 other than the region 1000 parallel in the axial direction (X-direction) to the region 102 in which the soft loading plate 20 is in contact with the core sample. In this case, as illustrated in FIG. 3, the position A may be the same as the first position described above, or may be the same as the first position and the second position.

Alternatively, according to an embodiment of the present disclosure, two or more strain measurement sensors (at least one of the attachment positions and the attachment direction being different from each other) may be attached to the position A. Alternatively, three or more strain measurement sensors (at least one of the attachment positions and the attachment direction being different from each other) may be attached to the position B.

One shape in which three or more strain measurement sensors are attached to the position B is illustrated in FIG. 3, and three strain measurement sensors 31, 32, and 33 having different strain measurement directions are attached to the position 3. In this case, the above-described explanation may be equally applied to a direction in which the strain is measured.

Alternatively, as an example in which the number of attached strain measurement sensors described above is three or more, as illustrated in FIG. 3, two or more strain measurement sensors may be attached to the position A included in the region 1000 parallel to the region 102 in the axial direction (X-direction) in which the soft loading plate 20 is in contact with the end surface 101 of the core sample, and one or more strain measurement sensors may be attached to the position B included in the area 2000 other than the parallel region 1000 (i.e., not included in the parallel region 1000). In this case, the strain measurement sensors attached to the position A may have at least one of an attachment position and an attachment direction different from each other.

Meanwhile, according to an embodiment of the present disclosure, in order to improve the accuracy of the measured elastic constant, the number of strain measurement sensors attached to the surface of the core sample may be 5 or more, or in some cases, the number thereof may be 7 or more.

As an embodiment of controlling the number of attached strain measurement sensors to five or more, the core sample may include positions A (1 and 2 of FIG. 3) in the region 1000 parallel to the region 102 in the axial direction (X-direction) to the region 102 in which the soft loading plate 20 is in contact with the end surface 101 of the core sample, and a position B that is not included in the parallel region 1000, and at least three strain measurement sensors (at least one of the attachment position and the attachment direction being different) are attached to at least one selected from the aforementioned positions A and B, and one or more strain measurement sensors may be attached to the remaining positions. For example, three strain measurement sensors (at least one of the attachment position and the attachment direction being different) are attached to at least one position selected from the positions A and B, and one strain measurement sensor is attached to the remaining position, and then, one or more strain measurement sensors may be additionally attached to at least one of the positions A and B so that at least one of the attachment position and the attachment direction is different from those of the already attached strain measurement sensor.

Alternatively, in another example, three or more strain measurement sensors may be attached to the position A (on a core sample surface (circumferential (Y) surface)) included in an area 1000 parallel to the axial direction (X-direction) with respect to the region 102 in which the soft loading plate 20 is in contact with the end surface 101 of the core sample. In addition, one or more strain measurement sensors 31, 32, and 33 having different strain measurement directions may be attached to the position B (on a core sample surface (circular direction (Y-direction) surface) not included in the region 1000 parallel to the region 102 in which the soft loading plate 20 is in contact with the end surface 101 of the core sample (or the position B included in the region 2000 other than the parallel region 1000).

Alternatively, in another embodiment in which the number of attached strain measurement sensors is five or more, in the position A, one or more strain measurement sensors 11 or 12 may be attached to a first position 1 (on the core sample surface (circumferential direction (Y-direction) surface)) a certain distance away from the end surface 101 of the core sample in the axial direction (X-direction). In this case, when two or more strain measurement sensors are attached to the first position, the strain measurement directions may be different from each other. Further, in the position A, one or more strain measurement sensors may be attached to a second position 2 further away from the end surface 101 of the core sample in the axial direction (X-direction) than the first position, and in this case, at least one of the strain measurement sensors attached to the second position may have the same direction as a direction in which the strain measurement direction is perpendicular to the axial direction (X-direction) (i.e., corresponding to 21 of FIG. 3). Meanwhile, although not particularly limited thereto, the measurement sensor attached to the B position and the strain measurement sensor attached to the second position may have the same shortest distance from the end surface 101 of the core sample in the axial direction (X-direction) (in this case, the above-mentioned shortest distance is measured based on a center of the strain measurement direction of each measurement sensor). Accordingly, as an embodiment in which the number of attached strain measurement sensors is five or more, in FIG. 3, the strain measurement sensor may be present in at least one of {(11) and (12)}, (21), (31), (32), and (33).

As an embodiment of controlling the number of attached strain measurement sensors to seven or more, two or more strain measurement sensors 11 and 12 may be attached to a first position 1 that is a certain distance away from the end surface 101 of the core sample in the axial direction (X-direction), which is included in the region 1000 parallel to the region 102 in which the soft loading plate 20 is in contact with the end surface 101 of the core sample, in the axial direction (X) (corresponding to the position A). Furthermore, two or more strain measurement sensors 21 and 22 may be attached to a second position 2 further away from the end surface 101 in the axial direction (X-direction) than the first position, which is included in the region 1000 parallel to the region 102 in which the soft loading plate 20 is in contact with the end surface 101 of the core sample, in the axial direction (X-direction) (corresponding to position A). Furthermore, three or more strain measurement sensors 31, 32, and 33 may be attached to a third position 3 included in the region 2000, that is not included in the region 1000 parallel to the axial direction (X-direction) with respect to the region 102 with which the soft loading plate 20 is contact.

In this case, when a plurality of strain measurement sensors are attached, at least one of the attachment positions and the attachment direction may be different from each other. In addition, although not particularly limited, the measurement sensor attached to the third position 3 and the strain measurement sensor attached to the second position 2 may have the same shortest distance from the end surface 101 of the core sample in the axial direction (X-direction) (in this case, the above-mentioned shortest distance is measured based on a center of the strain measurement direction of each measurement sensor). Accordingly, in an embodiment in which the number of attached strain measurement sensors is seven or more, in FIG. 3, the strain measurement sensor may be present in at least (11), (12), (22), (31), (32), and (33).

On the other hand, as described above, by controlling the number of strain measurement sensors and the number of attachment positions, the anisotropic elastic constants may be calculated with only a single core sample, and accordingly, time and costs may be drastically reduced, and the accuracy of the elastic constant estimated from the anisotropic material may be improved.

However, in the present disclosure, the number and position of attachments of the strain measurement sensors are not limited to the above-described form, but may be changed to various forms. In an example, various examples of changing the attachment position and number of the strain measurement sensors during a concentrated load test are illustrated in FIG. 5. FIG. 5 illustrates the attachment position of the strain measurement sensor on the y-axis in the concentrated load test according to a coring direction of the X-axis.

That is, after the soft loading plate 20 is in contact with only a portion of the end surface 101 of the core sample 100 described above, a concentrated load, a concentrated load, is applied in the axial direction (X-direction) of the core sample 100, on the soft loading plate 20, and then, a strain value is measured using the strain measuring sensor 10 (see FIG. 2B). A direction in which the above-described concentrated load is applied (corresponding to 'Load' of FIG. 2) may be the same as the axial direction (X-direction) of the core sample. In this case, except that the concentrated load is applied using the above-described soft loading plate 20, the concentrated load test method commonly known in the art may be equally applied to the present disclosure.

As described above, by applying a concentrated load test method that applies a concentrated load to the core sample 100 using the aforementioned soft loading plate 20, the elastic constant of the anisotropic material may be estimated relatively accurately even when a commonly known compressive loading machine is used without using additional testing equipment such as a loading machine with a specially controlled condition. That is, because the present disclosure may use a compressive loading machine and a strain measurement sensor used in a general test using a compressive load without any change so that the present disclosure can be realized without adding large costs.

Then, a step of obtaining the strain under the above-described load condition is followed. Specifically, while changing t elastic constant value, a computer numerical simulation test may be performed under the same load conditions as the one applied to the core sample, thus, the strain in the same position in which the strain was measured is calculated. Furthermore, when an error between the measured strain and the calculated strain is the lowest, the elastic constant value is determined as an elastic constant value of the core sample.

In an embodiment of the present disclosure, an elastic constant value obtained when the error falls within the allowable range may be set as elastic constant value of the core sample. In this case, the case that falls within the allowable range may denote that a size at which the error is reduced by the optimization test becomes smaller than a set limit error reducing rate, and the limit error reducing rate may be $0.5 \times 10\text{-}6$. That is, more accurate values may be obtained when finding the case with the smallest error, but as a correct elastic constant value is approached a reducing rate of error tends to decrease, and thus, there is no problem in selecting elastic constants that represent an error less than a limit of error reducing rate. However, when several elastic constants representing error reducing rate less than the limit error reducing rate are obtained, an elastic constant value representing the lowest error thereamong may be determined as an elastic constant value of the core sample.

Through the above-described computer numerical simulation test, it may be possible to find an optimal elastic constant that reproduces the measured strain. Since conventional methods mainly use explicit expressions, it was possible to calculate the elastic constant only for the test in an ideal situation, but according to the present disclosure, it may be possible to easily calculate the elastic constant for any experimental type. Through this computer numerical simulation test, a flowchart for determining an elastic constant value is schematically illustrated in FIG. 6. In the present disclosure, it may be possible to find an optimal value without knowing basically all elastic constants. However, since the better an initial value is selected, the shorter an estimation time of the elastic constant is, a method for estimating an elastic constant while using an estimated value of the elastic constant as an initial value may be used by applying an existing theory.

According to an embodiment of the present disclosure, in the computer numerical simulation test, equipment commonly used in the art, such as a program for computer numerical simulation of Comsol Multiphysics, may be used. According to the present disclosure, even if numerical analysis using complex expressions used in the existing method of calculating elastic constants is not applied, it may be possible to estimate the elastic constant relatively easily and accurately using a commonly used computer numerical simulation test.

Examples of elastic constants that may be calculated in the present disclosure may include a Young's modulus (E), a shear modulus (G), and a Poisson's ratio (v), and a conceptual diagram of such an elastic constant and a direction of an isotropic plane is illustrated in FIG. 7. On the other hand, when six or more strain measurement sensors are used, an angle between an isotropic plane 500 and the end portion 101 of the sample may also be estimated together with the elastic constant.

Meanwhile, according to an embodiment of the present disclosure, as compared to the existing methods for estimating elastic constants, the method of the present disclosure is economical and simple, and has a relatively low error rate, thereby making it possible to effectively estimate elastic constants with excellent accuracy.

Specifically, according to a method for estimating elastic constants of an anisotropic material according to an embodiment of the present disclosure, a numerical test may be performed on a heterogeneous sample in which an elastic constant is assigned for each element of 2 mm size to follow a normal distribution with a coefficient of variation of about 12%, and the Monte Carlo method may be applied. As a result of applying this method, as a relative error rate defined by the following relational expression 1, a Young's modulus may be 20% or less, and a shear modulus may be 10% or less, and a Poisson's ratio may be 0.1 or less in an error defined by the following relational expression 2.

$$\sqrt{\frac{1}{n}\sum_{i=1}^{n}\left(\frac{X_i - X_{true}}{X_{true}}\right)^2} \times 100\,(\%) \qquad \text{[Relationship 1]}$$

$$\sqrt{\frac{1}{n}\sum_{i=1}^{n}(X_i - X_{true})^2} \qquad \text{[Relationship 2]}$$

(In the relational expressions 1 and 2, $X_i$ represents a value of an optimal elastic constant estimated in an i-th iteration, $X_{true}$ represents a value of an elastic constant of an actual core sample, and n represents the total number of tests.)

Alternatively, according to an embodiment of the present disclosure, optionally, after the step of measuring the strain value, prior to the step of calculating the strain, an indirect tensile test may be additionally performed on a partial sample 200 additionally collected from the core sample.

Specifically, according to an embodiment of the present disclosure, the indirect tensile test may include a step of applying a load to both ends of the partial sample 200 in a diameter direction 50, and a step of measuring a strain value on a surface of the partial sample 200 to which the load is applied. A method of measuring such an indirect tensile test is schematically illustrated in FIG. 4.

In this case, according to an embodiment of the present disclosure, when measuring the strain value on the surface of the partial sample 200, after attaching two or more strain measurement sensors (71 and/or 72) to a surface 500 in an axial direction 60 of a column-shaped partial sample 200, the strain value at each attachment point may be measured.

In the indirect tensile test, there may be two or more strain measurement sensors 71 and 72 attached to an end surface of the partial sample, and in this case, at least one (one or more) of an attachment position and an attachment direction may be different from each other in at least one of the two or more strain measurement sensors. That is, the strain measurement sensors may be attached to the same attachment position so that the strain measurement directions are different from each other, or may be attached to different attachment positions.

Meanwhile, the above-described contents may be equally applied to the description of the measurement direction of the strain except for an indirect tensile test. Furthermore, the axial direction 60 of the partial sample 200 in the indirect tensile test may be consistent with the axial direction (X-direction) of the core sample in the above-described concentrated load test.

Meanwhile, in the present specification, except for the above-described contents, the conventional methods in the art may be equally applied to the indirect tensile test.

In the case of measuring the strain value by additionally performing the indirect tensile test, the strain may be calculated by the above-described method, and accordingly, an elastic constant value obtained when the error between the measured strain and the calculated strain is the lowest (or when the error falls within the allowable range) may be determined as an elastic constant value of the core sample. In this case, except for an indirect tensile test, the above-described contents may be equally applied to the description for the error, the elastic constant, and the like.

Following the concentrated load test, the indirect tensile test may be additionally performed, thereby further improving the accuracy of the estimated elastic constant from the anisotropic material. Accordingly, according to the method of estimating the elastic constant for the anisotropic material that has even been subjected to the indirect tensile test, as a result of performing the numerical tests described above and applying a Monte Carlo method, as a error relative rate defined by the aforementioned relational expression 1, the Young's modulus may be 8% or less and the shear modulus may be 8% or less, and the Poisson's ratio may be 0.05 or less as the error defined by the above-described relational expression 2.

According to the method of estimating the elastic constant of the present disclosure described above, the method may be sufficiently applied only with a single core sample collected from an anisotropic rock through a single coring, and also, since only low costs are required to manufacture a specially designed soft loading plate, time and costs may be greatly reduced, thereby making it very economically applicable. Accordingly, the present disclosure has considerable economic feasibility as compared to the existing methods.

Accordingly, according to the present disclosure, since the average elastic constant of an anisotropic material can be estimated economically and simply, the utilization of rocks covered in fields such as rock engineering, petroleum engineering, and resource engineering is high. In addition, since the present disclosure can be applied to various types of samples, the present disclosure may be widely applied in various fields such as construction environment engineering and material engineering.

MODE FOR INVENTION

Hereinafter, the present disclosure will be described in more detail through embodiments. However, it is necessary to note that the following embodiments are intended only to explain the present disclosure through examples, and are not intended to limit the scope of the present disclosure. This is because the scope of the present disclosure is determined by the matters described in the claims and matters reasonably inferred therefrom.

Inventive Example 1

After preparing Asan gneiss as an anisotropic material, by coring the rock, a cylindrical core sample with an axial length of 10.8 cm and a diameter of 5.4 cm was prepared. Then, a soft loading plate with a width of 5.4 cm, a length of 2.2 cm, and a height of 2 cm was prepared using Veroclear manufactured with a 3D printer. The soft loading plate was contacted so that only a portion of the end surface of either of both ends of the collected core sample was in contact.

After attaching a Kyowa's strain gauge to a surface (i.e., circumferential surface) except for the end surface of the core sample, in a different form as illustrated in FIG. 3 according to a coring angle to a normal line of an isotropic plane with a strain measuring sensor, a concentrated load was applied to the soft loading plate in the axial direction (X-direction) of the core sample using a compressive strength tester manufactured by MTS. Then, the strain value was measured with the strain measurement sensor, and while changing a value of an input elastic constant using the Comsol Multiphysics program, a computer numerical simulation test was performed under the same load condition as the one applied to the core sample, thus calculating a strain in the same position as a position in which the strain was measured. An elastic constant value was determined as an elastic constant value of the core sample when a sum of square of residuals between the plurality of measured strains and the plurality of calculated strains was the smallest. However, the Gauss-Newton method was used for optimizing the elastic constant, and a substitution method was used for angle optimization.

Inventive Example 2

Prior to performing the concentrated load test, a portion of the core sample was additionally cut in a radial direction to collect a partial sample with a length of 2.7 cm in the axial direction. Then, as illustrated in FIG. 4, two strain measurement sensors were attached to each of both surfaces of an end surface of the partial sample. Then, after performing an indirect tensile test in which a load was applied to the partial sample in the radial direction, the strain value was measured with the strain measurement sensor, and an elastic constant was obtained by the optimization using numerical analysis program in the same manner as Inventive Example 1 by adding the strain measured in Inventive Example 1.

Comparative Example 1

Using a conventional method, a core sample of the same shape was collected in the same manner as Inventive Example 1, two core samples were collected so that respective coring angles were 0° and 45°. For a sample with a coring angle of 0°, two strain measurement sensors in different directions were attached to the center of the sample, and for a sample with a coring angle of 45°, two strain measurement sensors with different strain measurement directions were attached to a position 3 of FIG. 3 and two strain measurement sensors with different strain measurement directions were attached to a position 2 of FIG. 3.

After performing a uniaxial compression test that applies a uniform load to both ends of each sample, a strain value was measured with the strain measurement sensor, and an elastic value determined by applying a constant relationship between strains and the elastic constants to a least squares method was determined as an elastic constant value of the core sample.

Table 1 below introduces a result of numerically reproduced heterogeneous rocks by allocating different elastic constants for each element of 2 mm size by normal distribution following the input value, and Monte Carlo analysis was performed using 100 different heterogeneous rocks which were reproduced numerically. From this, the accuracy of estimating the elastic constant to which the present technology is applied was evaluated in Inventive Examples 1 and 2 and Comparative Example 1 described above and is shown in Table 1 below. In this case, for comparison, as in Comparative Example 1, the elastic constant was estimated using two core samples collected in two directions, and the uncertainty of a coring angle $\varphi$ and a circumferential angle ($\theta$) of an isotropic plane was also considered.

The definitions of $E_1$, $E_2$, and $G_2$ mean a Young's modulus on an X-Z plane, a Young's modulus on a Y-axis, and a shear modulus on an X-Y or Y-Z plane, respectively, when the isotropic plane is disposed in parallel with the X-Z plane as shown in FIG. 7. $v_1$ is a first Poisson's ratio, which is a negative value of a ratio of the strain in the Z-axis direction to the strain in the X-axis when a uniaxial compression test in parallel with the X-axis is performed, and $v_2$ is a second Poisson's ratio, which is a negative value of a ratio of the strain in the Z-axis direction or X-axis direction to the Y-axis strain when a uniaxial compression test in parallel with the Y-axis is performed.

TABLE 1

| Division | | $E_1$ (GPa) | $E_2$ (GPa) | $G_2$ (GPa) | $v_1$ (—) | $v_2$ (—) | $\varphi$ (°) | $\theta$ (°) |
|---|---|---|---|---|---|---|---|---|
| Input Value | Estimation Value | 75 | 60 | 17 | 0.26 | 0.24 | 30 | 0 |
| | Error Rate | ±9.02 | ±6.98 | ±1.78 | ±0.0388 | ±0.0388 | ±2 | ±3 |
| Comparative Example 1 | Estimation Value | 73.82 | 59.98 | 17.05 | 0.2700 | 0.2400 | — | — |
| | Error Rate | ±3.15 | ±0.81 | ±0.18 | ±0.0257 | ±0.0089 | — | — |
| Inventive Example 1 | Estimation Value | 74.75 | 60.29 | 16.95 | 0.2680 | 0.2390 | 29.85 | — |
| | Error Rate | ±4.92 | ±2.39 | ±0.33 | ±0.1170 | ±0.0196 | ±2.98 | — |
| Inventive Example 2 | Estimation Value | 74.47 | 59.92 | 16.92 | 0.2635 | 0.2416 | 29.59 | |
| | Error Rate | ±1.12 | ±1.35 | ±0.26 | ±0.0118 | ±0.0057 | ±2.38 | — |

As can be seen from the testing results of Table 1, in the case of Comparative Example 1 using the conventional method, since a core sample in two directions is essential, excessive time and costs are required.

On the other hand, in the case of Inventive Examples 1 and 2 of the present application, compared to Comparative Example 1, since an error range for the elastic constant is ensured on an acceptable level using only a single core sample, it has been confirmed that time and costs can be effectively reduced.

Specifically, in the case of Inventive Example 2 of the present application, as described above, it was confirmed that not only time and costs can be effectively reduced, but also accuracy can be ensured to a level similar to that of Comparative Example 1 using the conventional method in terms of accuracy of the elastic constant.

Meanwhile, in the case of Inventive Example 1 of the present application, the error was somewhat larger than that of Inventive Example 2, but considering the time and costs saved using only a single sample, it was evaluated to have high usability.

DESCRIPTION OF REFERENCE CHARACTERS

100: Core Sample
X: Axial Direction of Core Sample
Y: Circumferential Direction of Core Sample
10: Strain Measurement Sensor
20: Soft loading plate
101: End surface of Core Sample (or axial (X-direction) surface)
102: Region in contact with the soft loading plate 20 on the end surface 101 of the core sample
103: Region not in contact with the soft loading plate 20 on the end surface 101 of the core sample
1, 2 and 3: Position in which the strain measurement sensor
11, 12, 21, 22, 31, 32 and 33: Strain Measurement Sensor
71 and 72: Strain Measurement Sensor 200: Partial Sample
50: In an indirect tensile test, a diameter direction of the partial sample 200
60: In the indirect tensile test, an axial direction of the partial sample 200
300: Surface of an axial direction 60 of the partial sample 200
500: Isotropic plane of the core sample
600: A curve formed by the isotropic plane 500 of the core sample on the circumferential surface (i.e., a surface other than both end surfaces of the core sample)
71 and 72: Strain Measurement Sensor
1000: Region, parallel to the region 102 in which the soft loading plate 20 is in contact with the core sample, in the axial direction (X-direction)
2000: Region other than the region 1000, parallel to the region 102 in which the soft loading plate 20 is in contact with the core sample, in the axial direction (X-direction)

The invention claimed is:

1. A method for estimating elastic constants, comprising:
collecting a core sample from an anisotropic material;
applying a load to respective ends of the core sample;
measuring a strain value on a surface of the core sample to which the load is applied;
calculating a strain in the same position as a position in which the strain was measured by performing a computer numerical simulation test under the same load condition applied to a core sample while changing an input elastic constant value; and
determining an elastic constant value when an error between the measured strain and the calculated strain is the lowest, as an elastic constant value of the core sample,
wherein at least one of the load applied to respective ends of the core sample is a concentrated load applied only to a portion of a surface of an end.

2. A method for estimating elastic constants, comprising:
collecting a core sample from an anisotropic material;
applying a load to respective ends of the core sample;
measuring a strain value on a surface of the core sample to which the load is applied;
calculating a strain in the same position as a position in which the strain was measured by performing a computer numerical simulation test under the same load condition applied to a core sample while changing an input elastic constant value; and
determining a value of an elastic constant obtained when the error between the measured strain and the calculated strain falls within an allowable range, as an elastic constant value of the core sample,
wherein at least one of the load applied to respective ends of the core sample is a concentrated load applied only to a portion of a surface of an end.

3. The method for estimating the elastic constants of an anisotropic material of claim 1, wherein only a single sample is used as the core sample.

4. The method for estimating the elastic constants of an anisotropic material of claim 1, wherein the core sample has a columnar shape.

5. The method for estimating the elastic constants of an anisotropic material of claim 1, wherein a soft loading plate is provided so as to come into contact with only a portion of an end surface to which the load is applied.

6. The method for estimating the elastic constants of an anisotropic material of claim 5, wherein a Young's modulus of the soft loading plate is $\frac{1}{10}$ or less as compared to a Young's modulus of the core sample.

7. The method for estimating the elastic constants of an anisotropic material of claim 1, wherein in the measuring a strain value, a strain measurement sensor is attached to the surface of the core sample to measure a strain value at each attachment point,
when attaching the strain measurement sensor, one or more strain measurement sensors are attached to a first position a certain distance away from an end surface of the core sample in an axial direction, and
one or more additional strain measurement sensors are attached to a second position further away from the end surface of the core sample in the axial direction than the first position.

8. The method for estimating the elastic constants of an anisotropic material of claim 5, wherein in the measuring a strain value, a strain measurement sensor is attached to the surface of the core sample to measure a strain value at each attachment point,
one or more strain measurement sensors are attached to a position A included in a region parallel to an axial direction with respect to a region in which the soft loading plate is in contact with an end surface of the core sample, and
one or more additional strain measurement sensors are attached to a position B not included in a region parallel to the axial direction with respect to the region in which the soft loading plate is in contact with the end surface of the core sample.

9. The method for estimating the elastic constants of an anisotropic material of claim 8, wherein two or more strain measurement sensors in which one or more of an attachment position and an attachment direction is different from each other are attached to the position A.

10. The method for estimating the elastic constants of an anisotropic material of claim 5, wherein in the measuring a strain value, a strain measurement sensor is attached to the surface of the core sample to measure a strain value at each attachment point, the core sample comprises a position A included in a region parallel to an axial direction with respect to a region in which the soft loading plate is in contact with the end surface, and a position B not included in a region parallel to the axial direction with respect to the region in which the soft loading plate is in contact with the end surface, and three or more strain measurement sensors in which one or more of an attachment position and an attachment direction is different from each other are attached to at least one position selected from the position A and the position B, and one or more strain measurement sensors are attached to a remaining position.

11. The method for estimating the elastic constants of an anisotropic material of claim 1, wherein the number of strain measurement sensors attached to the surface of the core sample is 5 or more.

12. The method for estimating the elastic constants of an anisotropic material of claim 8, wherein in the position A, one or more strain measurement sensors are attached to a first position a certain distance away from the end surface of the core sample in the axial direction, and in the position A, one or more strain measurement sensors are attached to a second position further away from the end surface of the core sample in the axial direction (X-direction) than the first position.

13. The method for estimating the elastic constants of an anisotropic material of claim 1, further comprising:

after the measuring a strain value, prior to the calculating a strain, performing an indirect tensile test on a partial sample additionally collected from the core sample.

14. The method for estimating the elastic constants of an anisotropic material of claim 1, wherein as a relative error rate defined by the following relational expression 1, a Young's modulus satisfies 20% or less, and a shear modulus satisfies 10% or less, and an error for a Poisson's ratio defined by the following relational expression 2 satisfies 0.1 or less, $$\sqrt{\frac{1}{n}\sum_{i=1}^{n}\left(\frac{X_i - X_{true}}{X_{true}}\right)^2} \times 100\,(\%) \qquad \text{[Relational Expression 1]}$$

$$\sqrt{\frac{1}{n}\sum_{i=1}^{n}(X_i - X_{true})^2} \qquad \text{[Relational Expression 2]}$$

(in the relational expressions 1 and 2, $X_i$ represents a value of an optimal elastic constant estimated in the i-th test, $X_{true}$ represents a value of an elastic constant for an actual core sample, and n represents the total number of tests).

15. The method for estimating the elastic constants of an anisotropic material of claim 13, wherein as a relative error rate defined by the following relational expression 1, a Young's modulus satisfies 8% or less, and a shear modulus satisfies 8% or less, and an error for a Poisson's ratio defined by the following relational expression 2 satisfies 0.05 or less, $$\sqrt{\frac{1}{n}\sum_{i=1}^{n}\left(\frac{X_i - X_{true}}{X_{true}}\right)^2} \times 100\,(\%) \qquad \text{[Relational Expression 1]}$$

$$\sqrt{\frac{1}{n}\sum_{i=1}^{n}(X_i - X_{true})^2} \qquad \text{[Relational Expression 2]}$$

(in the relational expressions 1 and 2, $X_i$ represents a value of an optimal elastic constant estimated in the i-th test, $X_{true}$ represents a value of an elastic constant for an actual core sample, and n represents the total number of tests).

* * * * *